US006626915B2

(12) United States Patent
Leveillee

(10) Patent No.: US 6,626,915 B2
(45) Date of Patent: Sep. 30, 2003

(54) MEDICAL RETRIEVAL DEVICE WITH LOOP BASKET

(75) Inventor: Raymond J. Leveillee, Cooper City, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/298,423

(22) Filed: Apr. 22, 1999

(65) Prior Publication Data

US 2001/0049535 A1 Dec. 6, 2001

Related U.S. Application Data

(60) Provisional application No. 60/105,448, filed on Oct. 23, 1998, and provisional application No. 60/082,810, filed on Apr. 23, 1998.

(51) Int. Cl.[7] .............................................. A61B 17/24
(52) U.S. Cl. ..................... 606/114; 606/113; 606/127
(58) Field of Search ............................... 606/114, 110, 606/113, 115, 127, 128, 159, 160, 158, 200

(56) References Cited

U.S. PATENT DOCUMENTS

| 651,395 A | 6/1900 | Strapp |
| 1,054,960 A | 3/1913 | Butner |
| 2,556,783 A | 6/1951 | Wallace .................. 128/321 |
| 2,767,703 A | 10/1956 | Nieburgs |
| 3,791,387 A | 2/1974 | Itoh ........................ 128/320 |
| 3,828,790 A | 8/1974 | Curtiss et al. ............. 128/320 |
| 3,955,578 A | 5/1976 | Chamness et al. ..... 128/303.15 |
| 4,198,960 A | 4/1980 | Utsugi ......................... 128/6 |
| 4,326,530 A | 4/1982 | Fleury, Jr. ............. 128/303.14 |
| 4,427,014 A | 1/1984 | Bel et al. ................... 128/751 |
| 4,590,938 A | 5/1986 | Segura et al. ............. 128/328 |
| 4,655,219 A | 4/1987 | Petruzzi .................... 128/321 |
| 4,691,705 A | 9/1987 | Okada ....................... 128/328 |
| 4,718,419 A | 1/1988 | Okada .................. 128/303.15 |
| 4,807,626 A | 2/1989 | McGirr ..................... 128/328 |
| 4,893,621 A | 1/1990 | Heyman ..................... 128/328 |
| 4,994,079 A | 2/1991 | Genese et al. ............ 606/206 |
| 5,010,894 A | 4/1991 | Edhag ....................... 128/785 |
| 5,011,488 A | 4/1991 | Ginsburg ................... 606/159 |
| 5,057,114 A | 10/1991 | Wittich et al. ............ 606/127 |
| 5,064,428 A | 11/1991 | Cope et al. ................ 606/127 |
| 5,084,054 A | 1/1992 | Bencini et al. ............ 606/113 |
| 5,098,440 A | 3/1992 | Hillstead .................. 606/108 |
| 5,147,378 A | 9/1992 | Markham .................. 606/206 |
| 5,163,942 A | 11/1992 | Rydell ....................... 606/113 |
| 5,171,233 A | 12/1992 | Amplatz et al. ........... 604/281 |
| 5,171,314 A | 12/1992 | Dulebohn .................. 606/113 |
| 5,207,686 A | 5/1993 | Dolgin ....................... 606/113 |

(List continued on next page.)

FOREIGN PATENT DOCUMENTS

| CH | 480059 A | 12/1969 |
| DE | 2804058 | 8/1978 |
| DE | 3522649 A1 | 1/1986 |
| DE | 3501707 | 7/1986 |
| DE | 4212430 A | 10/1993 |
| EP | 0123175 A | 10/1984 |
| SU | 1228837 | 5/1986 |
| WO | 92/05828 | 4/1992 |
| WO | 95/05129 | 2/1995 |
| WO | 98/36694 | 8/1998 |

OTHER PUBLICATIONS

Copy of International Search Report in PCT/US99/08487.

Primary Examiner—Pedro Philogene
(74) Attorney, Agent, or Firm—Testa, Hurwitz & Thibeault LLP

(57) ABSTRACT

Baskets with atraumatic distal tips allow the capture of material from difficult-to-reach areas of the body, while reducing the risk of tissue damage.

11 Claims, 2 Drawing Sheets

U.S. PATENT DOCUMENTS

| | | | |
|---|---|---|---|
| 5,290,294 A | 3/1994 | Cox et al. | 606/108 |
| 5,365,926 A | 11/1994 | Desai | 128/642 |
| 5,376,100 A | 12/1994 | Lefebvre | 606/180 |
| 5,417,684 A | 5/1995 | Jackson et al. | 606/1 |
| 5,421,832 A | 6/1995 | Lefebvre | 604/53 |
| 5,454,370 A | 10/1995 | Avitall | 128/642 |
| 5,462,553 A | 10/1995 | Dolgin | 606/113 |
| 5,486,183 A | 1/1996 | Middleman et al. | 606/127 |
| 5,549,661 A | 8/1996 | Kordis et al. | 607/99 |
| 5,613,973 A | 3/1997 | Jackson et al. | 606/113 |
| 5,632,746 A | 5/1997 | Middleman et al. | 606/78 |
| 5,647,870 A | 7/1997 | Kordis et al. | 606/41 |
| 5,693,069 A | 12/1997 | Shallman | 606/205 |
| 5,725,525 A | 3/1998 | Kordis | 606/41 |
| 5,810,876 A | 9/1998 | Kelleher | 606/205 |
| 5,823,189 A | 10/1998 | Kordis | 128/642 |
| 5,846,238 A | 12/1998 | Jackson et al. | 606/41 |
| 5,853,411 A | 12/1998 | Whayne et al. | 606/41 |
| 6,099,534 A * | 8/2000 | Bates et al. | 606/127 |
| 6,174,318 B1 * | 1/2001 | Bates et al. | 606/114 |
| 6,224,612 B1 * | 5/2001 | Bates et al. | 606/114 |

* cited by examiner

MEDICAL RETRIEVAL DEVICE WITH LOOP BASKET

CROSS-REFERENCE TO RELATED APPLICATIONS

This application is based on and claims priority to provisional U.S. patent application Ser. No. 60/082,810 which was filed on Apr. 23, 1998, and U.S. provisional patent application Ser. No. 60/105,448 which was filed on Oct. 23, 1998.

TECHNICAL FIELD

The invention relates generally to medical devices for retrieving material from within a body. More particularly, the invention relates to medical retrieval baskets that have atraumatic distal ends that are contoured or tipless both to minimize the chances of damage to tissue during use and to enhance the ability of the basket to capture material (e.g., stones) disposed or lodged in "pockets" or other areas that are difficult to access in the body.

BACKGROUND INFORMATION

Known stone retrieval devices typically have baskets that are constructed by joining multiple legs together at a base of the basket and at a distal end or tip of the basket such that a "cage" is formed. At the distal tip, the individual legs are joined by soldering, adhesives, etc. such that a protruding tip results. This protrusion or outward projection at the distal end of the basket can poke tissue and cause tissue trauma. In general, the tips or ends of known baskets protrude outward and thus can cause damage by poking or piercing tissue. Also, the protruding tips of known baskets generally do not permit access to or intimate contact with certain areas within the body such as "pockets," and thus stones residing in such areas are difficult or impossible to retrieve with known baskets.

SUMMARY OF THE INVENTION

It is an object of the invention to provide a medical retrieval basket that does not have a substantially protruding distal basket end or basket tip. That is, a basket according to the invention is atraumatic and does not have any significant distal protrusion or outward projection that can poke tissue, pierce tissue, or otherwise cause trauma to tissue.

It is another object of the invention to provide a medical retrieval basket that permits access to and/or intimate contact with certain areas within the body such as "pockets" where material to be retrieved (e.g., stones) might reside or be lodged, impacted, or embedded. A tipless or contoured tip basket arrangement can access these areas and retrieve material from those areas whereas a conventional basket with a traumatic tip would not be able to do so because of the traumatic protruding tip that prevents intimate contact between the distal end of the basket and body tissue.

It is yet another object of the invention to provide a method of using such baskets to retrieve material from within a body. The material can be biological or foreign matter. The material can be, for example, urological stones or any of a variety of other types of material found in the body.

A basket according to the invention is formed by a plurality of wires, each wire forming a loop. Thus, the basket according to the invention is tipless and atraumatic, and lacks a protruding distal tip.

The invention generally relates to a medical retrieval device. The device comprises a sheath, a handle, and an atraumatic basket. The sheath has a proximal end and a distal end. The handle is located at the proximal end of the sheath. The basket can remove material from a body, and it is moveable between a collapsed position when the basket is enclosed within the sheath and an expanded position when the basket is extended from the distal end of the sheath. The basket has four or more legs (e.g., six, or eight legs). At least a distal end portion of the atraumatic basket is tipless and formed by a plurality of wires, each wire forming a loop. The apex of each of the loops is positioned at the distal end of the basket. The ends of each loop are attached to one another at the basket base or to an elongated member. The loops are unattached and freely moveable at the distal end of the basket.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1A:
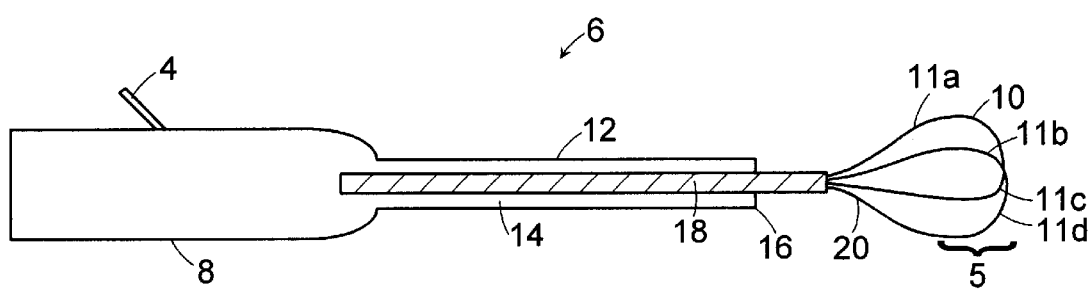
FIG. 1A illustrates one embodiment of a medical retrieval device with an atraumatic basket according to the invention with the basket in an expanded position.
Figure 1B:
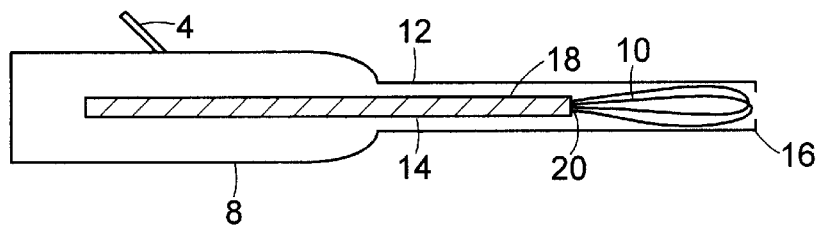
FIG. 1B illustrates one embodiment of a medical retrieval device with an atraumatic basket according to the invention with the basket in a collapsed position.

The basket 10 shown in FIG. 1A is the type that can be collapsed within a sheath 12 for entry into the body. A medical device or extractor 6 that includes the basket 10 of the invention also includes the sheath 12 and a proximal handle 8. The handle 8, sheath 12 and basket 10 illustrated in FIGS. 1A and 1B are not shown in their correct size or proportion to each other. The sheath 12 has at least one lumen 14 therein, and it extends from the handle 8 to a distal sheath end 16. An elongated member such as a cable, coil, shaft, guidewire or mandril wire 18 extends within the lumen 14 from an actuating mechanism 4 at the device handle 8 to the base 20 of the basket 10 where the cable 18 is attached to the basket base 20. Operation of the actuating mechanism 4 by an operator causes the basket 10 to move relative to the sheath 12 between a collapsed position within the sheath 12 as illustrated in FIG. 1B to an extended position outside of the sheath 12 where the basket 10 is open/expanded and extending beyond the distal end of the sheath 16 as shown in FIG. 1A. Alternatively, the mechanism 4 can cause movement of the sheath 12 to advance the sheath 12 over the stationary basket 10 and cable 18 combination, to thereby collapse the basket 10 within the sheath 12, and the mechanism 4 can slide the moveable sheath 12 back to expose the stationary basket 10 and allow it to open/expand. In general, both types of basket/sheath movement configurations and related handle mechanisms are known, and can be seen in existing product designs available from, for example, Boston Scientific Corporation (Natick, Mass.). With the basket withdrawn into and collapsed within the sheath 12 as shown in FIG. 1B, the sheath 12 can be inserted into the body by an operator to a site in the body where the material to be retrieved is located (e.g., a stone in the ureter). The basket 10 is then moved relative to the sheath 12 and placed in the extended position, as illustrated in FIG. 1A, such that the basket 10 dilates the body tract and can be manipulated by the operator to entrap or capture material within the basket 10. The basket 10 can then be moved relative to the sheath 12 to cause the legs 11a, 11b, 11c, 11d of the basket 10 to close around the material and capture it. The captured material is then withdrawn from the body along with the sheath and the basket that is holding the material.

Figure 2A:
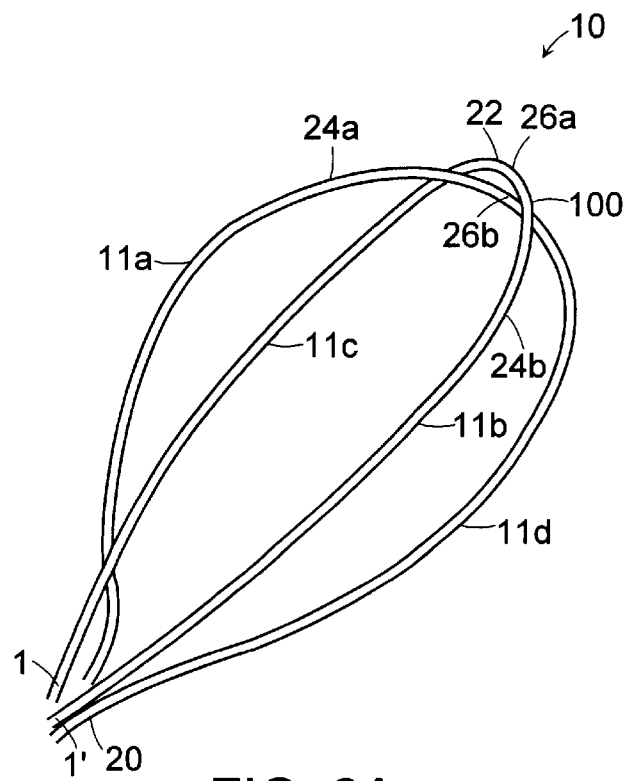
FIG. 2A illustrates an embodiment according to the invention of a basket formed by a plurality of loops, the loops being unattached where the loops intersect at the distal end of the basket.
Figure 2B:
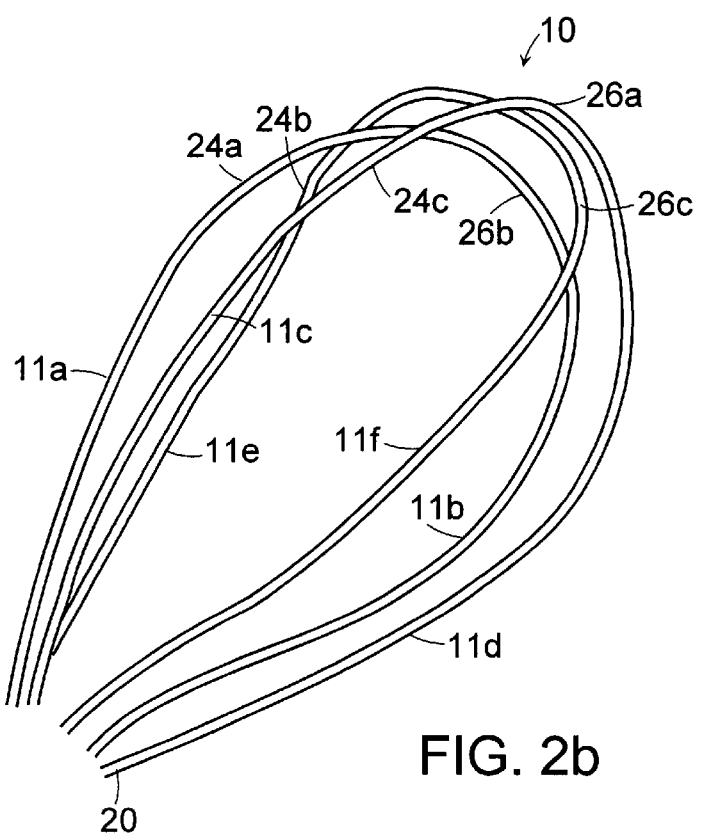
FIG. 2B illustrates an embodiment according to the invention of another embodiment of the basket illustrated in FIG. 2A comprising more than two basket loops.

Referring to FIGS. 2A and 2B, a tipless end 22 of the atraumatic basket 10 is constructed by using single wires to form loops 24a, 24b having legs 11a, 11b, 11c, 11d extending from the apex 26a, 26b of the loops 24a and 24, respectively, the apex 26a, 26b positioned at the basket distal end 22. A plurality of pre-formed wire loops is included in a three-dimensional, atraumatic basket. In this embodiment of an atraumatic wire basket, for example, two wire loops 24a, 24b may be used to form a basket with four legs 11a, 11b, 11c, 11d as shown in FIG. 2A, and three wire loops 24a, 24b, 24c may be used to form a basket with six legs 11a, 11b, 11c, 11d, 11e, 11f as shown in FIG. 2B. Additional wire loops may be used to form a basket with more than the four or six legs shown. The apex 26 of each wire loop 24 intersects the apex 26 of the other wire loops 24 of the basket 10 at the basket distal end 22. The wire loops 24 at the basket distal end are free to slide by one another, i.e., they are not affixed, fused, soldered, welded, glued, joined, secured or attached to one another. The advantages of this configuration of the basket distal end 22 is that the basket end 22 is atraumatic and provides flexibility thereby enhancing the ease by which stones are captured. The two end-sections 1, 1' of each wire loop are brought together at the basket base 20 and held in place by welding, soldering, ligating, gluing, crimping or any other means known in the art. In one embodiment, the end-sections 1, 1' of the wire loops are affixed (not shown) to a cable, coil, shaft, mandril wire or guidewire 18 that runs longitudinally in a sheath 12 as shown in FIG. 1A and FIG. 1B.

In yet another aspect, the invention relates to a method for retrieving material from a body such as a body tract or body canal. Material (e.g., biological or foreign) can be retrieved from a body by using a tipless, atraumatic wire basket, each wire forming a loop and having an atraumatic distal basket end according to the invention. The basket of the retrieval device has an atraumatic distal end and thus allows the capture of material that is located in pockets or other difficult-to-access areas within the body. Because the distal basket end is atraumatic, it can make intimate contact with the surface of tissue, even the walls or lining of a pocket-type area, and allow the retrieval of stones or other materials that are unrecoverable with conventional tipped baskets that can cause tissue trauma and are limited in how close the basket can get to the tissue by the existence of the protruding tip. A method for retrieving material from a body includes inserting a retrieval device according to the invention into the body, moving the tipless basket into the extended position, maneuvering the basket via the proximal handle (which is located outside of the body) of the retrieval device until the material (e.g., stone) is entrapped within the three-dimensional basket structure, and then capturing the material within the basket by moving the basket relative to the sheath to close the basket legs around the material. With the material so gripped or held by the basket, the basket can be withdrawn from the body to remove the material from the body. The materials that can be captured with tipless baskets according to the invention include a calculus, or a stone, such as a kidney stone, a ureteral stone, a urinary bladder stone, a gall bladder stone, or a stone within the biliary tree.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical retrieval device, comprising:

a sheath having a lumen, proximal end, and a distal end;

a handle at the proximal end of the sheath; and an atraumatic basket for atraumatically removing material from a body, the basket having a collapsed position where the basket is enclosed within the sheath and an expanded position where the basket extends from the distal end of the sheath, the basket comprising two or more pairs of basket legs, each pair of basket legs formed from a single wire loop, and each pair of said basket legs crossing each other and being unattached and freely moveable with respect to each other at a distal end of the basket when said basket is in the collapsed position or the expanded position.

2. The medical device of claim 1 wherein said basket comprises three pairs of basket legs.

3. The medical device of claim 1 wherein said sheath is movable over the basket, wherein said basket is in the collapsed position when the sheath is advanced over the basket, and said basket is in the expanded position when the sheath is retracted from the basket.

4. The medical device of claim 1 further comprising an elongated member, said elongated member axially moveable in said sheath lumen, said basket joined at a proximal end of said basket to the distal end of sa elongated member, wherein axial movement of said elongated member moves said basket between the expanded position and the collapsed position.

5. A method for retrieving material from a body, comprising:

inserting a retrieval device into said body, the retrieval device comprising a sheath having a proximal end and a distal end, a handle at the proximal end of the sheath, and an atraumatic basket for atraumatically removing material from a body, the basket having a collapsed position where the basket is enclosed within the sheath, and an expanded position where the basket extends from the distal end of the sheath, the basket comprising two or more pairs of basket legs, each pair of basket legs formed from a single wire loop, and each pair of said basket legs crossing each other and being unattached and freely moveable with respect to each other at a distal end of the basket when said basket is in the collapsed or the expanded position;

atraumatically capturing the material within the basket; and withdrawing the retrieval device from the body to remove the captured material from the body.

6. The method of claim 2 wherein said material retrieved from said body comprises a kidney stone.

7. The method of claim 2 wherein said material retrieved from said body comprises a ureteral stone.

8. The method of claim 2 wherein said material retrieved from said body comprises a urinary bladder stone.

9. The method of claim 2 wherein said material retrieved from said body comprises a urethral stone.

10. The method of claim 1 wherein said material retrieved from said body comprises a gall bladder stone.

11. The method of claim 2 wherein said material retrieved from said body comprises a biliary stone.

* * * * *

UNITED STATES PATENT AND TRADEMARK OFFICE
CERTIFICATE OF CORRECTION

PATENT NO. : 6,626,915 B1 Page 1 of 1
DATED : September 30, 2003
INVENTOR(S) : Leveillee It is certified that error appears in the above-identified patent and that said Letters Patent is hereby corrected as shown below:

Column 4,
Line 40, replace "sa" with -- said --;
Line 64, replace "2" with -- 5 --;

Column 5,
Line 1, replace "2" with -- 5 --;
Line 3, replace "2" with -- 5 --;
Line 5, replace "2" with -- 5 --;

Column 6,
Line 3, replace "2" with -- 5 --.

Signed and Sealed this

Thirtieth Day of March, 2004

JON W. DUDAS
*Acting Director of the United States Patent and Trademark Office*